US00PP09304P

United States Patent [19]

Machin

[11] Patent Number: Plant 9,304

[45] Date of Patent: Sep. 26, 1995

[54] CHRYSANTHEMUM PLANT NAMED 'BRONZE MAJESTY'

[75] Inventor: Barrie J. Machin, Hants, England

[73] Assignee: Goldstock Breeding Limited, Hants, England

[21] Appl. No.: 254,266

[22] Filed: Jun. 3, 1994

[51] Int. Cl.[6] ..... A01H 5/00

[52] U.S. Cl. ..... Plt./82.3

[58] Field of Search ..... Plt./82.3, 74.1

[56] References Cited

U.S. PATENT DOCUMENTS

| | | | |
|---|---|---|---|
| P.P. 3,906 | 6/1976 | Jessel, Jr. et al. | Plt./82.3 |
| P.P. 6,903 | 7/1989 | Van den Berg | Plt./82.3 |
| P.P. 8,769 | 6/1994 | van der Jagt | Plt./82.3 |
| 4,616,099 | 10/1986 | Sparkes | 47/58 |

OTHER PUBLICATIONS

Broertjes, et al., 1980, "Amutant of a Mutant of a . . . Irradiation of Progressive Radiation–Induced Mutants in a Mutation Breeding Programme with *Chrysanthemum morifolium*", Euphytica, 29:526–530.

Gosling, ed., 1979, "The Chrysanthemum Manual–6th edition", The National Chrysanthemum Society, London, Essex Telegraph Press, Ltd., pp. 329–336.

Broertjes, et al., 1978, "Application of Mutation Breeding Methods in the Improvement of Vegetatively Propagated Crops", Elsevier Sci. Pub. Co., New York, pp. 162–175.

Searle, et al., 1968, "Chrysanthemums the Year Round", Blanford Press, London, pp. 27–29, 320–327.

Chan, 1966, "Chrysanthemum and Rose Mutations Induced by X–Rays", Am. Soc. Hort. Sci. Proc., pp. 613–620.

Broertjes, 1966, "Mutation Breeding of Chrysanthemums", Euphytica, 15:156–162.

Dowrick, et al., 1966, "The Induction of Mutations in Chrysanthemum Using X– and Gamma Radiation", Euphytica, 15:204–210.

*Primary Examiner*—Howard J. Locker
*Attorney, Agent, or Firm*—Foley & Lardner

[57] ABSTRACT

A new Chrysanthemum cultivar named Bronze Majesty characterized by the combined features of flat capitulum form, daisy capitulum type, bronze floret color, capitulum diameter of 66–76 mm, a response period of 59–63 days when grown with 14 long days prior to start of short days, a plant height of 90–100 cm, and an inverted pyramid flower formation.

3 Drawing Sheets

The present invention comprises a new and distinct cultivar of Chrysanthemum, botanically known as *Dendranthema grandiflora,* and referred to by the cultivar named Bronze Majesty.

Bronze Majesty is a mutation of Majesty which originated from a cross made by the inventor Barrie J. Machin in a controlled breeding program in Fareham, England in 1986. The parent cultivar is disclosed in application Ser. No. 08/139,009, now U.S. Plant Pat. No. 8,944.

Bronze Majesty is a product of a mutation induction program carried out by the inventor in Fareham, England. The program had the objective of creating new cultivars that would expand the ray floret color range of Majesty, which has very light pink ray floret color.

Bronze Majesty was discovered and selected by Barrie J. Machin in April 1988 in Wareham, England as one flowering plant within a flowering block established as rooted cuttings from plants of Majesty that had been exposed as unrooted cuttings to an X-ray source of 1500 rads.

The first act of asexual reproduction of Bronze Majesty was accomplished when vegetative cuttings were taken from the initial selection in June 1988 in a controlled environment in Fareham, England by Barrie J. Machin.

Horticultural examinations of controlled flowerings of successive plantings has shown that the unique combination of characteristics as herein disclosed from Bronze Majesty are firmly fixed and are retained through successive generations of asexual reproduction.

Bronze Majesty has not been observed under all possible environmental conditions. The phenotype may vary somewhat with variations in environment such as temperature, light intensity and day length, without, however, any variance in genotype.

The following observations, measurements and comparisons describe plants of Bronze Majesty grown in Fareham, England under greenhouse conditions which approximate those generally used in commercial greenhouse practice.

The following traits have been repeatedly observed and are determined to be basic characteristics of Bronze Majesty which in combination distinguish this Chrysanthemum as a new and distinct cultivar.

1. Flat capitulum form.
2. Daisy capitulum type.
3. Bronze ray floret color.
4. Diameter across face of capitulum of 66–76 mm when fully open.
5. Flowering response under normal temperatures is 59 to 63 days after start of short days.
6. Peduncle length of the first lateral at flowering after removal of the apical bud and without growth regulator applications is 9.0 cm, and the peduncle length of the fourth lateral at flowering is 12.0 cm.
7. Plant height of 90–100 cm.

The accompanying photographic drawings show typical inflorescence and leaf characteristics of Bronze Majesty, with the colors being as nearly true as possible with illustrations of this type.

The color photograph on sheet 1 illustrates flower and foliage colors of Bronze Majesty grown as a cut spray mum.

The black and white photo on sheet 2 illustrates three views of the inflorescence of Bronze Majesty.

The black and white photo on sheet 3 shows the upper and under surfaces of the leaves of Bronze Majesty at three stages of development.

Of the commercial cultivars known to the inventor the most similar in comparison to Bronze Majesty is the unpatented cultivar identified as Bronze Marble. Reference is made to attached chart A which compares certain characteristics of Bronze Majesty with the same characteristics of Bronze Marble. Similar traits are capitulum form and type, response and spray formation. The bronze ray floret color of Bronze Majesty is substantially darker than Bronze Marble, and Bronze Majesty has a slightly smaller capitulum diameter, is slightly shorter and has shorter peduncles.

In comparison to the parent cultivar Majesty, the ray floret color of Bronze Majesty is completely different, Bronze Majesty has a slightly smaller capitulum diameter, and the plant height of Bronze Majesty is slightly shorter. All other characteristics are the same or comparable.

In the following description, color references are made to The Royal Horticultural Society Color Chart. The color values were determined on plant material of Bronze Majesty grown as a single spray cut mum in Fareham, England.

Classification:

*Botanical.*—*Dendranthema grandiflora* cv Bronze Majesty.

*Commercial.*—Daisy spray cut mum.

Inflorescence

A. Capitulum

*Form.*—Flat.

*Type*—Daisy.

*Diameter across face.*—66–76 mm.

B. Corolla of ray florets:

*Color (general).*—Bronze.

*Color (upper surface).*—24A.

*Color (under surface).*—23B.

*Shape.*—Broad, pointed and slightly curved.

C. Corolla of disc florets:

*Color (mature).*—13A.

*Color (immature).*—143C.

*Quantity.*—Approximately 200 per flower.

D. Reproductive organs:

*Androecium.*—Present only on disc florets; small quantity of pollen.

*Gynoecium.*—Present in disc and ray florets.

Plant

A. General appearance:

*Height.*—90–100 cm.

*Branching pattern.*—Regular branching habit, typically one branch developing per leaf axil.

B. Foliage:

*Color (upper surface).*—147A.

*Color (under surface).*—147B.

*Shape.*—Pinnately lobed with deep marginal indentations; see photograph on sheet 3.

CHART A

| CHARACTERISTICS | BRONZE MAJESTY | BRONZE MAJESTY |
|---|---|---|
| Ray floret color | Bronze | Light Bronze |
| Capitulum form and type | flat daisy | flat/daisy |
| Diameter across face of capitulum | 66–76 mm | 70–80 mm |
| Plant height | 90–100 cm | 95–105 cm |
| Peduncle length | | |
| 1st lateral | 9 cm | 11 cm |
| 4th lateral | 12 cm | 14 cm |
| Spray formation | Inverted pyramid | Inverted pyramid |

It is claimed:

1. A new and distinct Chrysanthemum plant named Bronze Majesty, as described and illustrated.

* * * * *

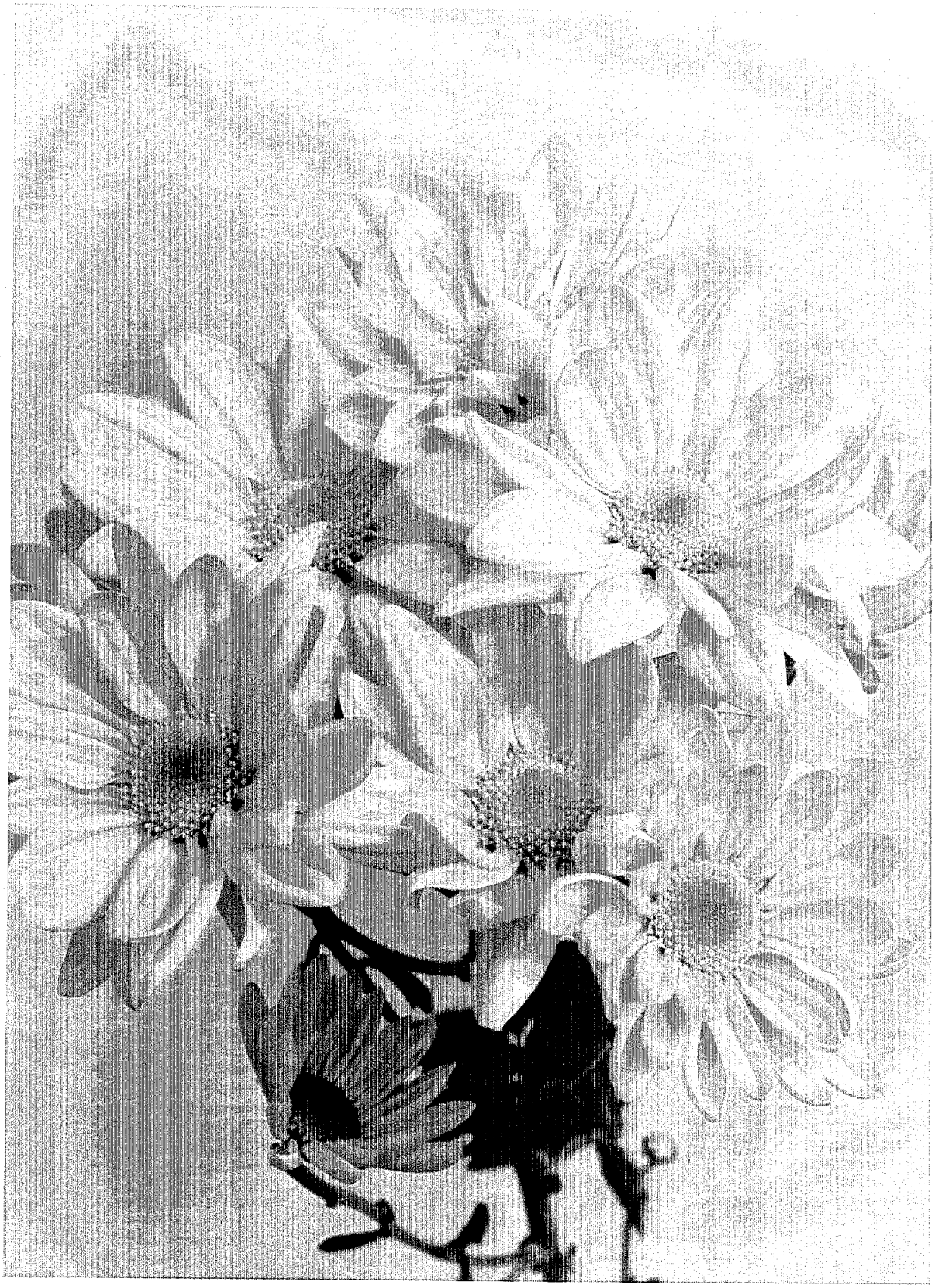

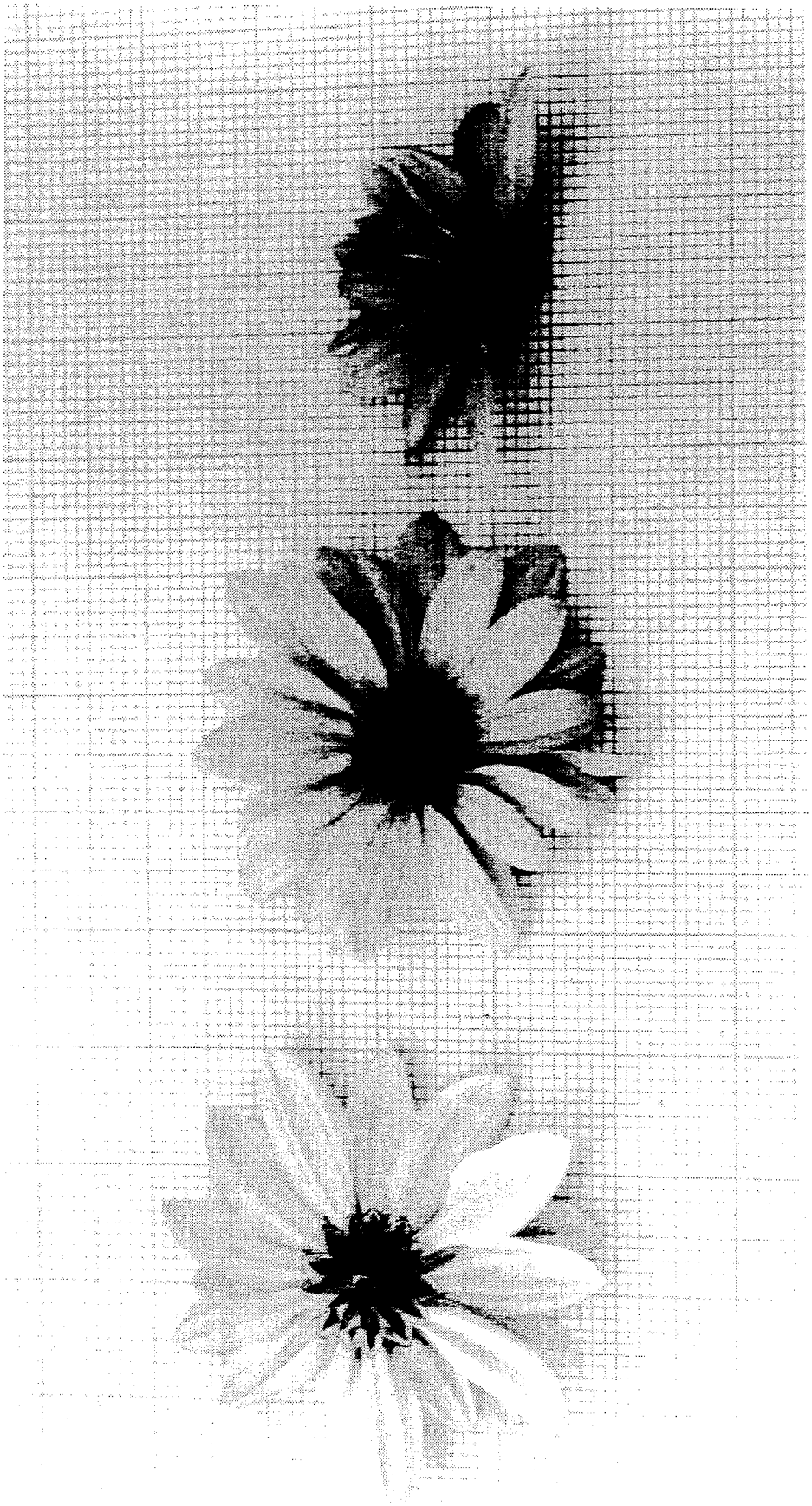

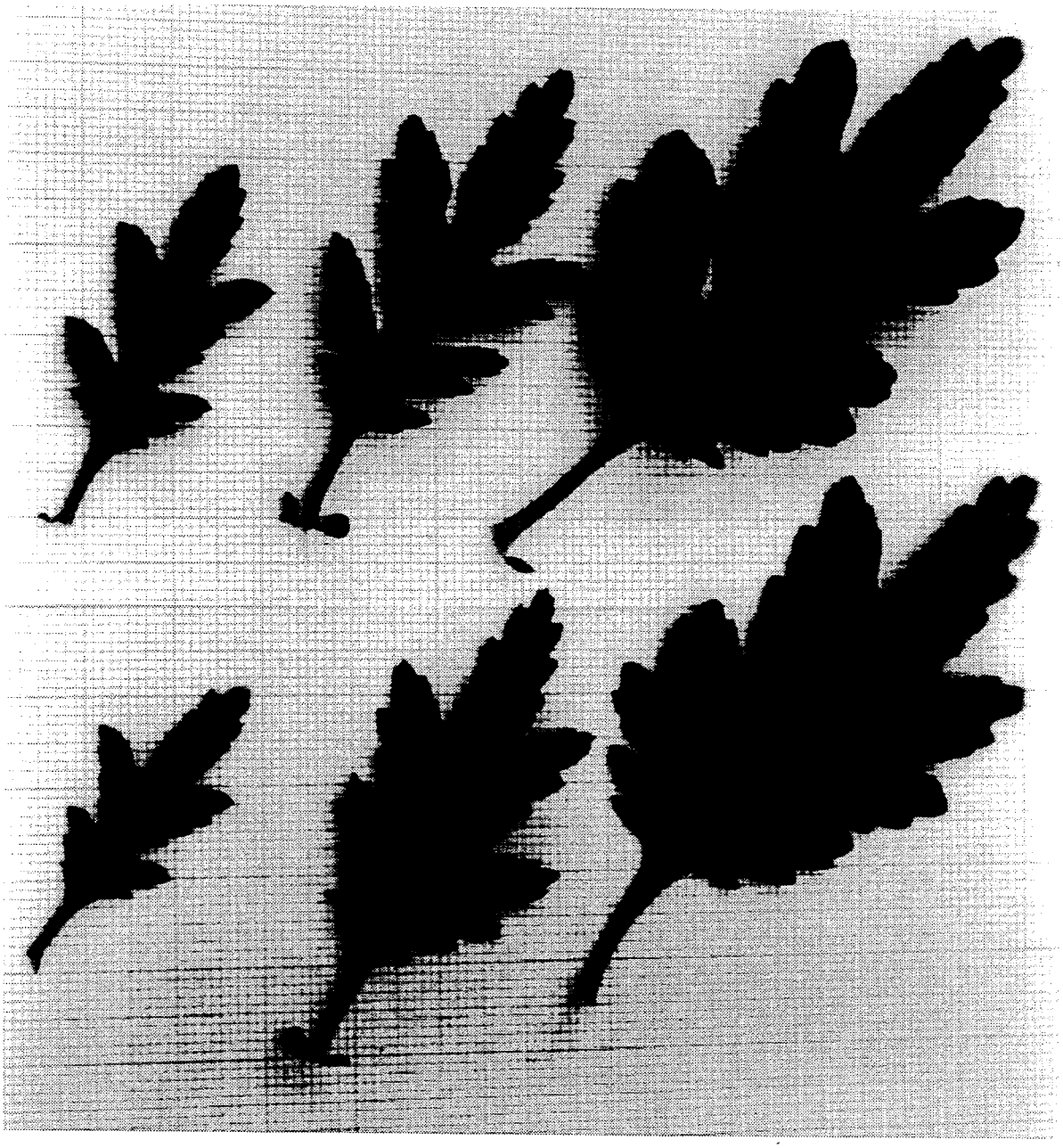

UNITED STATES PATENT AND TRADEMARK OFFICE

CERTIFICATE OF CORRECTION

PATENT NO. : Plant 9,304

DATED : September 26, 1995

INVENTOR(S) : MACHIN

It is certified that error appears in the above-indentified patent and that said Letters Patent is hereby corrected as shown below:

Column 1, line 10, "8,944" should read --8,994--;

line 17, "Wareham" should read --Fareham--.

Signed and Sealed this

Twentieth Day of February, 1996

*Attest:*

*Attesting Officer*

BRUCE LEHMAN

*Commissioner of Patents and Trademarks*